(12) United States Patent
Hwang et al.

(10) Patent No.: US 10,342,427 B2
(45) Date of Patent: Jul. 9, 2019

(54) ELECTRONIC APPARATUS AND THE CONTROL METHOD THEREOF

(71) Applicant: Samsung Electronics Co., Ltd., Suwon-si, Gyeonggi-do (KR)

(72) Inventors: Tae-ho Hwang, Seoul (KR); Mi-young Kim, Suwon-si (KR); Min-sung Jang, Seoul (KR); Hang-ho Lee, Seoul (KR); Min-su Hwangbo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 217 days.

(21) Appl. No.: 15/213,864

(22) Filed: Jul. 19, 2016

(65) Prior Publication Data
US 2017/0196456 A1    Jul. 13, 2017

(30) Foreign Application Priority Data
Jan. 8, 2016    (KR) ........................ 10-2016-0002392

(51) Int. Cl.
*A61B 5/00*    (2006.01)
*A61B 5/0205*    (2006.01)
(Continued)

(52) U.S. Cl.
CPC .......... *A61B 5/0024* (2013.01); *A61B 5/0205* (2013.01); *A61B 5/0402* (2013.01);
(Continued)

(58) Field of Classification Search
CPC ... A61B 5/0024; A61B 5/0205; A61B 5/0402; A61B 5/0476; A61B 5/4809; A61B 5/6803; A61B 5/681; A61B 5/6815
See application file for complete search history.

(56) References Cited

U.S. PATENT DOCUMENTS 6,238,338 B1    5/2001    Deluca et al.
8,469,862 B2    6/2013    Andren et al.
(Continued)

FOREIGN PATENT DOCUMENTS

KR    10-2008-0084879 A    9/2008
KR       10-1521539 B1    5/2015
(Continued)

OTHER PUBLICATIONS

International Search Report dated Nov. 2, 2016, issued in PCT/KR2016/007872.

*Primary Examiner* — Paula J Stice
(74) *Attorney, Agent, or Firm* — Jefferson IP Law, LLP

(57) ABSTRACT

An electronic apparatus which is capable of being worn on a user's body is provided. The electronic apparatus includes first and second wearing units configured to connect to each other, the first wearing device including a first measurer configured to measure the user's body, and a first communicator configured to communicate with the second wearing device, and the second wearing device including a second measurer configured to measure a user's body, and a second communicator configured to communicate with the first wearing device, and a at least one main processor configured to process a first measurement signal generated by using the first measurer while the first and second wearing devices are connected to each other, and to process a second measurement signal measured and generated by the second measurer while the first and second wearing devices are either connected to each other or disconnected from each other.

17 Claims, 20 Drawing Sheets

(51) Int. Cl.
  *A61B 5/0402* (2006.01)
  *A61B 5/0476* (2006.01)
  *A61B 5/0488* (2006.01)
  *A61B 5/024* (2006.01)
  *A61B 5/053* (2006.01)

(52) U.S. Cl.
  CPC .......... *A61B 5/0476* (2013.01); *A61B 5/0488* (2013.01); *A61B 5/4809* (2013.01); *A61B 5/681* (2013.01); *A61B 5/6803* (2013.01); *A61B 5/7282* (2013.01); *A61B 5/7405* (2013.01); *A61B 5/7425* (2013.01); *A61B 5/02416* (2013.01); *A61B 5/0533* (2013.01)

(56) References Cited

U.S. PATENT DOCUMENTS

| | | |
|---|---|---|
| 2005/0261564 A1 | 11/2005 | Ryu et al. |
| 2007/0042821 A1 | 2/2007 | Lee et al. |
| 2008/0043575 A1 | 2/2008 | Fasciano |
| 2014/0140567 A1* | 5/2014 | LeBoeuf ............... A61B 5/7221 |
| | | 381/381 |
| 2015/0172429 A1 | 6/2015 | Cai et al. |
| 2015/0181324 A1 | 6/2015 | Hsieh et al. |
| 2016/0339300 A1* | 11/2016 | Todasco .................. H04W 4/80 |
| 2017/0086732 A1* | 3/2017 | Tribble ................ A61B 5/4809 |

FOREIGN PATENT DOCUMENTS

| | | |
|---|---|---|
| KR | 10-1564073 B1 | 10/2015 |
| KR | 10-2015-0126268 A | 11/2015 |
| WO | 2015/167318 A1 | 11/2015 |

\* cited by examiner

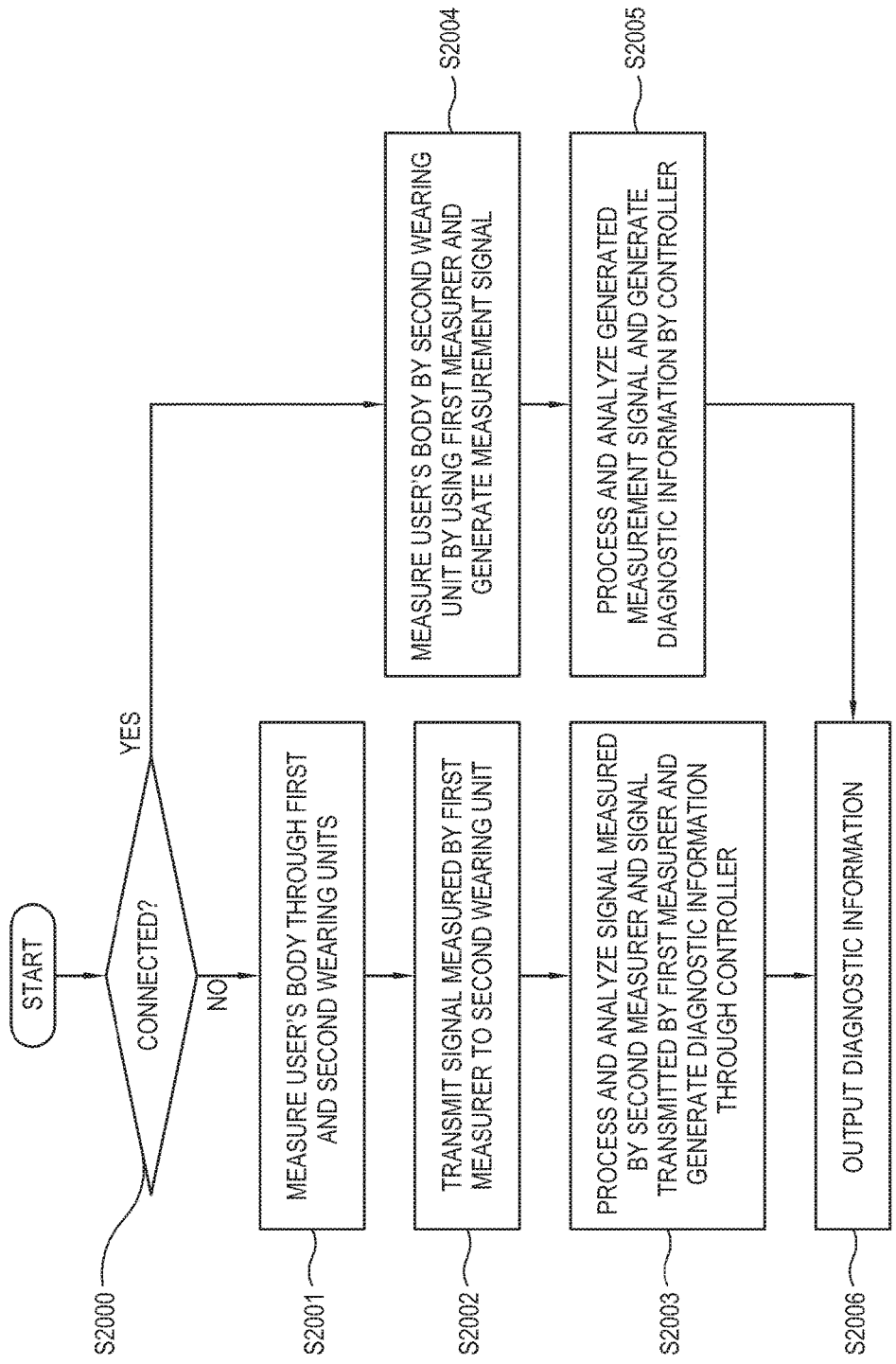

ELECTRONIC APPARATUS AND THE CONTROL METHOD THEREOF

CROSS-REFERENCE TO RELATED APPLICATION(S)

This application claims the benefit under 35 U.S.C. § 119(a) of a Korean patent application filed on Jan. 8, 2016 in the Korean Intellectual Property Office and assigned Serial number 10-2016-0002392, the entire disclosure of which is hereby incorporated by reference.

TECHNICAL FIELD

The present disclosure relates to an electronic apparatus which a user may wear, and which has a plurality of wearing units that is connectable to each other and disconnectable from each other. More particularly, the present disclosure relates to an electronic apparatus which is worn on a plurality of body parts of a user and measures and analyzes a user's vital sign(s), provides a user information on a result of the analysis of the vital sign(s) when disconnected from each other, and uses resources by sharing a circuit when connected to each other.

BACKGROUND

In line with development of science, medical technology is continuously developing. Various areas of health care services are provided for improvement of health, and health care services are developing into a medical service for monitoring user's biological information and health information and preventing and treating diseases.

To monitor a user's health information, the smart health market provides various wearable devices, and applications and platforms for analyzing collected information are under development.

As health care devices are emerging, people are paying attention to a technology for measuring and using a user's vital sign such as a brain wave and electrocardiogram (ECG) using a portable device such as a wearable device as well as for measuring a body motion of a user.

While the wearable device has a strength of using data that has been collected for a long time by measuring a vital sign in a daily life as well as a strength of portability, but has the problem of less accurate vital signs since the measured area is limited to a wearable area such as wrist and thus a device can measure a vital sign of only one body part of a user. If a user uses a plurality of wearable devices simultaneously and if the wearable devices have batteries differing in size and power consumption and are not compatible with one another, he/she may feel inconvenient in recharging each of the batteries and storing one of the devices when not in use.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic apparatus and a control method thereof including a plurality of connectable and disconnectable wearing units.

In accordance with an aspect of the present disclosure, an electronic apparatus which is capable of being worn on the user's body is provided. The electronic apparatus includes a first wearing device and a second wearing unit configured to connect to each other, the first wearing device including a first measurer configured to measure a user's body, and a first communicator configured to communicate with the second wearing device, and the second wearing device including a second measurer configured to measure a user's body, and a second communicator configured to communicate with the first wearing device, and at least one main processor configured to process a first measurement signal generated by using the first measurer while the first wearing unit and the second wearing unit are connected to each other, and to process a second measurement signal measured and generated by the second measurer while the first wearing unit and the second wearing unit are either connected to each other or disconnected from each other.

Each of the first and second measurers may include a sensor configured to generate a sensing signal by measuring the user's body, and a sub-processor configured to process the sensing signal to generate at last one of the first and second measurement signals.

The sub-processor may include an amplifier configured to amplify the sensing signal.

The vital sign may include at least one of electroencephalogram (EEG), electrocardiogram (ECG), photo plethysmography (PPG), electromyogram (EMG), and galvanic skin reflex (GSR).

The electronic apparatus may further include an output portion configured to output information.

The output portion may be provided in at least one of the first and second wearing units.

The output portion may include a display configured to display an image corresponding to the information.

The output portion may include a speaker configured to output sound corresponding to the information.

The at least one main processor may be further configured to analyze the user's health status based on at least one of the first and second measurement signals and generate diagnostic information, and controls the output portion to provide the generated diagnostic information.

The diagnostic information may include a user's sleeping status.

The at least one main processor may control the output portion to warn that the user is in sleep.

Each of the first and second communicators may include a terminal to supply or receive power, and the controller may control the first and second communicators to exchange power between the first wearing device and the second wearing device if the first wearing device and second wearing device are connected to each other.

The at least one processor may control the output portion to provide a user interface (UI) including menu items for a user to change setting information of the electronic apparatus.

At least one of the first and second communicators may be capable of communicating with an external device.

The at least one processor may control the output portion to provide information transmitted from the outside.

The at least one processor may generate user authentication information based on the first and second measurement signals.

The at least one processor may control at least one of the first and second communicators to transmit the authentication information to an external device in response to a request for authentication from the external device.

In accordance with another aspect of the present disclosure, a control method of an electronic apparatus which is capable of being worn on a user's body is provided. The electronic apparatus includes measuring the user's body through first and second wearing units, performing communication between the first wearing device and second wearing device, processing a first measurement signal generated through a first measurer while the first and second wearing units are connected to each other, and processing a second measurement signal measured by a second measurer while the first wearing device and the second wearing device are either connected to each other or disconnected from each other.

The measuring the user's body may include generating a sensing signal by measuring the user's body, and generating at least one of the first and second measurement signals by processing the sensing signal.

The processing the sensing signal may include amplifying the sensing signal.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 20 is a flowchart of controlling the electronic apparatus according to an embodiment of the present disclosure.

Throughout the drawings, like reference numerals will be understood to refer to like parts, components, and structures.

DETAILED DESCRIPTION

Figure 1:
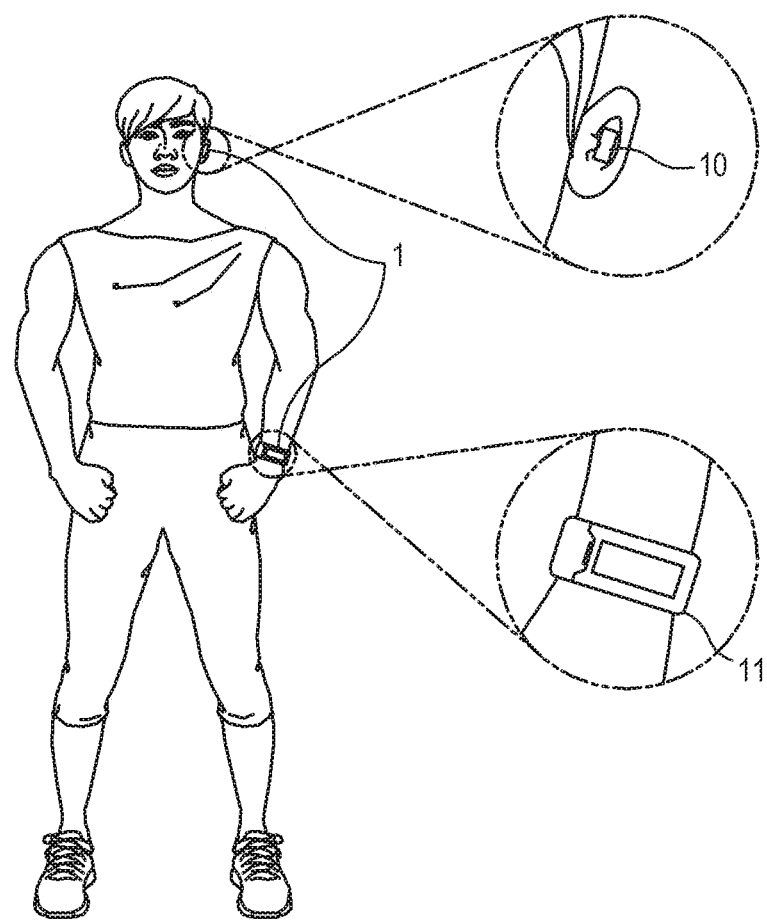
FIG. 1 illustrates an example of an electronic apparatus including a plurality of wearing units according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Some of the elements shown in accompanying drawings have been exaggerated, omitted or briefly illustrated, and the size of each element does not wholly reflect the actual size. The present disclosure is not limited by the relative size or interval shown in accompanying drawings.

If an element is described as "including" another element throughout this specification, it means the former may further include the latter rather than excluding other elements unless otherwise specifically provided herein. The term "portion" used in this specification means software field-programmable gate array (PFGA) or hardware such as application-specific integrated circuit (ASIC), and may be configured to perform certain roles. However, the term "portion" is not limited to the software or hardware, and may be configured to be in an addressable storage medium, or may be configured to reproduce one or more processors. Thus, as an example, the term "portion" includes elements such as software elements, object-oriented software elements, class elements and task elements, and processes, functions, features, procedures, sub-routines, segments of program codes, drivers, firmware, micro codes, circuits, data, database, data configurations, tables, arrays and variables. The functionality provided in the elements and or portions may be coupled to a smaller number of elements and parts or further divided into additional elements and portions.

With reference to accompanying drawings, embodiments of the present disclosure will be described in detail for those skilled in the art to work the present disclosure without difficulty. The present disclosure may be achieved in various forms, and are not limited to the embodiments provided herein. To clearly describe the present disclosure, those unrelated to the description have been omitted, and like reference numerals denote like elements throughout this specification.

In this specification, an electronic apparatus may be configured to measure a user's vital sign when worn by a user, to analyze a user's health status based on a measured sign, and provide a user with analyzed health information. For such purpose, the electronic apparatus may include a plurality of wearing units which is configured to be worn on a plurality of a user's body parts.

In this specification, the wearing unit is an apparatus to be worn on a part of a user's body and to measure a user's vital sign, and may be achieved as a separate device from the electronic apparatus or as being provided in the electronic apparatus.

In this specification, the vital sign is a variation of a sound or electric potential that is generated according to a repeated motion within a body of the measured target at the surface of the body of the measured target, and means a sign that is generated according to a motion of the body and has a plurality of periods.

In this specification, the measurement signal means a signal that has a waveform generated on the basis of the measured vital sign and is generated corresponding to characteristics of the vital sign.

In this specification, the health information means information relating to a user's health status analyzed on the basis of the measured vital sign of a user and may be used as diagnostic information or health information herein.

Below, embodiments of the present disclosure will be described with reference to accompanying drawings.

FIG. 1 illustrates an example of an electronic apparatus 1 including a plurality of wearing units according to an embodiment of the present disclosure.

Referring to FIG. 1, an electronic apparatus 1 according to the present disclosure may include a first wearing unit 10 which is worn on a user's first body part, and a second wearing unit 11 which is worn on a user's second body part. FIG. 1 illustrates an example of the first wearing unit 10 which is achieved by a wireless earphone worn on user's ears and the second wearing unit 11 which is achieved by a smart watch worn on a user's wrist, but the present disclosure is not limited to the smart watch and the earphone. The electronic apparatus 1 may be configured to analyze a user's health status based on a vital sign measured by the first and second wearing units 10 and 11, and to provide a user with information based on the analyzed health status. It should be understood that the terms "device(s)" and "unit(s)" are used interchangeably and connote a structure as known in the art.

For example, the electronic apparatus 1 may be configured to measure a user's brain wave, to determine whether a user is sleeping or focused based on the measured brain wave and to provide information on the user's status as determined above. Also, the electronic apparatus 1 may be configured to output a warning or a particular content based on a user's status.

A brain wave is a vital sign showing the activity of a human brain. If the brain is active, a potential difference is caused by ions, e.g. sodium ions or potassium ions that pass through cell membranes in the cranial nerve. A flow of weak electricity that is generated from the potential different is the brain wave. A brain tissue is surrounded by a conductive medium and a current generated from a neuron may be transmitted to the surface of the head, and therefore the brain wave can be measured through an electrode attached to the scalp. The brain wave may be classified as delta wave (~3 Hz), theta wave (4 Hz~8 Hz), alpha wave (8 Hz~12 Hz), beta wave (12 Hz~30 Hz), and gamma wave (26 Hz~100 Hz) according to a frequency of a waveform.

The electronic apparatus 1 may be configured to monitor an electrical activity of the brain based on a signal measured below the head, rather than to directly measure a user's brain wave. The signal measured below the head is called a raw signal, and a brain wave which is analyzed through the raw signal is called a body wave. A body wave is an electrophysiological signal such as ECG, and may be classified as theta wave (4 Hz~8 Hz), alpha wave (8 Hz~12 Hz) and beta wave (12 Hz~30 Hz), similarly to a brain wave. That is, the measuring portion of the electronic apparatus 1 does not need to be positioned in the head area of a user, and may be positioned in, e.g. a wrist of a user to measure a user's brain activity.

The electronic apparatus 1 in this embodiment is not limited to a smart watch or earphone shown in drawings and description. The electronic apparatus 1 may be achieved by various types of devices that may measure and analyze a user's vital sign, including a mobile phone, tablet personal computer (PC), person digital assistant (PDA), kiosk, navigator, digital television (TV), smart glass, and head-mounted display (HMD).

Below, for convenience, the first wearing unit 10 and the second wearing unit 11 will be described as an earphone worn on user's ears and as a smart watch worn on a user's wrist, respectively, in this specification unless otherwise described.

Figure 2:
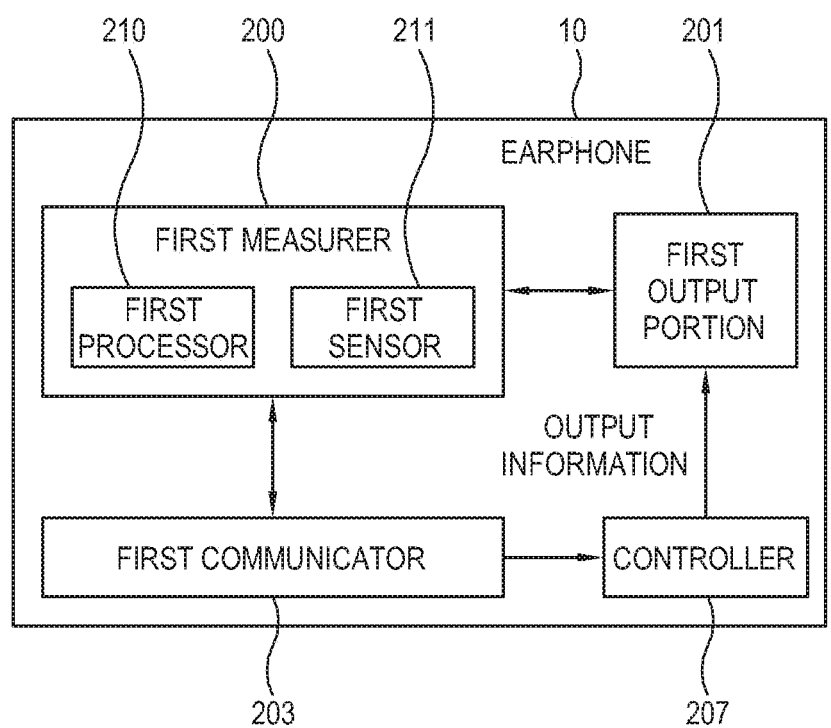
FIG. 2 is a block diagram of a first wearing unit according to an embodiment of the present disclosure.

FIG. 2 is a block diagram of the first wearing unit 10 according to an embodiment of the present disclosure.

Figure 3:
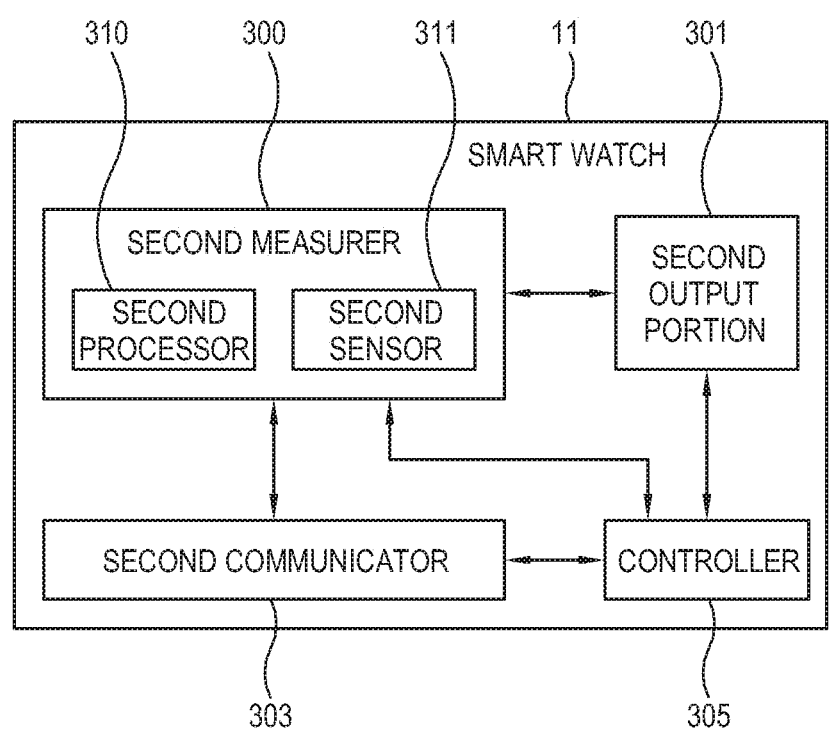
FIG. 3 is a block diagram of a second wearing unit according to an embodiment of the present disclosure.

FIG. 3 is a block diagram of the second wearing unit 11 according to an embodiment of the present disclosure. In the drawings and embodiments as provided below, each of elements of the electronic apparatus 1 may be arranged separately in physical form or logical form, or may be combined into a single element.

Referring to FIG. 3, the first wearing unit 10 according to an embodiment of the present disclosure may be configured to be worn on a user's first body part, to measure a vital sign and to transmit a measured vital sign to the second wearing unit 11. For such purpose, the first wearing unit 10 includes a first measurer 200, a first communicator 203 and a controller 207. The first wearing unit 10 may further include a first output portion 201 for providing a user with information. If the first wearing unit 10 is achieved by an earphone, the first output portion 201 may include a speaker to provide information as an audio or sound.

The second wearing unit 11 according to an embodiment of the present disclosure may be configured to be worn on a user's second body part and to measure a vital sign, and to analyze a measured vital sign, which is received by the first wearing unit 10, together with the first wearing unit 10 to thereby analyze a user's health status. For such purpose, the second wearing unit 11 according to an embodiment of the present disclosure includes a second measurer 300, a second communicator 303 and a controller 305. The second wearing unit 11 may further include a second output portion 301 to provide a user with information. If the second wearing unit 11 is achieved by a smart watch, the second output portion 301 may be configured to include a display to provide information as an image.

The measurers 200 and 300 are configured to measure a user's vital sign and generate a measurement signal. A vital sign which may be measured by the measurers 200 and 300 may include a brain wave, pulse wave, electrocardiography, etc. The measurers 200 and 300 may further include sensors 211 and 311 to measure a vital sign. The sensors 211 and 311 may obtain at least one of electroencephalogram (EEG), electrooculogram (EOG), electrocardiogram (ECG) and electromyogram (EMG) signals in the case of a brain wave. The sensors 211 and 311 may obtain a vital sign by being closely adhered to a user's body. The sensors 211 and 311 used may vary depending on a type of a vital sign to be measured. The measurers 200 and 300 may further include processors 210 and 310 to process the signal measured by the sensors 211 and 311. Signal processing includes modulation, demodulation, multiplexing and other various signal conversions for using the measured signal, and may further include amplification to be made to make the signal measured from a body available.

The first measurer 200 may include a first sensor 211 including an electrode to measure a user's brain wave from the inside of a user's ear or from a user's forehead and to generate a measurement signal, and a first processor 210 to process the measured signal. The second measurer 300 may include a second sensor 311 including an electrode to measure a part of a user's body to measure a user's body wave from a user's body part from the head and therebelow, and a second processor to process a measured signal. The second measurer 300 may generate a measurement signal based on its measurement.

The measurer 300 may be configured to measure various information including heartbeat, pulse wave and motion as well as a body wave and brain wave, and corresponding thereto may include various sensors 211 and 311. The processors 210 and 310 may further include an amplifier to amplify a measured vital sign to an available level within the electronic apparatus 1.

The first measurer 200 is configured to directly measure a user's brain wave, and may include the first sensor 211 and the first processor 210 which have higher performance than the second measurer 300 does. If the first and second wearing units 10 and 11 are connected to each other, the first measurer 200 may be used to measure the body and generate a measurement signal by a control of the controller 305.

The communicators 203 and 303 are configured to communicate with an external device to thereby transmit signal provided by the outside. The communicators 203 and 303 may include a connection port to be connected to an external device directly or through a signal line for communication. The connection port may employ various methods corresponding to specifications of signals transmitted and received thereby or a method of achievement. For example, the connection port may be a connector suitable for a data pin of a signal which is manufactured to transmit various image signals including high definition multimedia interface (HDMI), digital visual interface (DVI), display data channel (DDC) and auxiliary (AUX). The communicators 203 and 303 may include a radio frequency (RF) circuit to transmit and receive an RF signal for wireless communication. The communicators 203 and 303 may perform wireless communication through a wireless network such as wireless local area network (LAN) or wireless fidelity (Wi-Fi), and may perform wireless communication with an external device through Bluetooth (BT). The communicators 203 and 303 may further perform communication for internet telephone and exchange of messages.

The communicators 203 and 303 may include a power transmission and reception terminal to provide power to an external device connected thereto, and may be configured to share battery power with an external device depending on a connection or disconnection of the power transmission and reception terminal.

The output portions 201 and 301 are configured to provide a user with various information. The output portions 201 and 301 may include one of a speaker to output sound or audio, and a display to output an image. The output portions 201 and 301 may be provided in at least one of the first wearing unit 10 and the second wearing unit 11. For example, the first wearing unit 10 may be achieved by an earphone to be worn on user's ears, and may include the first output portion 201 to output a sound or audio. The second wearing unit 11 may be achieved by a smart watch to be worn on a user's wrist, and may include the second output portion 301 to provide a character or image.

The speaker may include an internal speaker to provide an audio regarding a user's health status as analyzed or to output a warning sound if a user's health is not normal. The display displays health information in a screen.

The controllers 207 and 305 are configured to control overall operations of the electronic apparatus 1. More specifically, the controllers 207 and 305 may control the first and second measurers 200 and 300 to measure a user's body part on which the first wearing unit 10 and the second wearing unit 11 are worn and to generate a measurement signal when the first and second wearing units 10 and 11 are disconnected from each other, and may control the first and second measurers 200 and 300 to measure a user's body part on which the first and second wearing units 10 and 11 are worn and to generate a measurement signal when the first and second wearing units 10 and 11 are connected to each other, and may process the measurement signal generated as above. The connection of the first and second wearing units 10 and 11 means a physical connection therebetween. For example, the first wearing unit 10 as an earphone may be connected to the second wearing unit 11 as a smart watch to generate a vital sign from a user' wrist wearing the smart watch, and generate a measurement signal by using elements of the first wearing unit 10. The first measurer 200 may include the first sensor 211 or the first processor 210 which has higher performance than the second sensor 311 and the second processor 310 of the second measurer 300 do. By the connection of the first and second wearing units 10 and 11, a vital sign may be more precisely measured from a user's body part on which the second wearing unit 11 is worn.

The controllers 207 and 305 may process a generated measurement signal, and determine a user's health status by analyzing the processed measurement signal. More specifically, the controllers 207 and 305 may be configured to detect an electrical activity of a user's brain based on a body wave measured by the second measurer 300. As described above, as the second measurer 300 is configured to measure and process a body wave as a potential change within the body based on brain activity, the controllers 207 and 305 may detect a user's brain activity through analysis, e.g. comparison of a measurement signal generated by the second measurer 300 and a user's brain wave measured by the first measurer 200. The controllers 207 and 305 may generate health information or diagnostic information by analyzing a user's health status such as sleeping, focused, tired and stressed statuses based on the user's brain activity detected as above.

A user's health status is a status which may be analyzed based on a measured vital sign such as whether a user is sleeping or stressed or a user has an unstable brain wave. The controller 305 may control the output portions 201 and 301 to provide diagnostic information concerning a diagnosis of a user's heath based on the analyzed status. The health information or diagnostic information may be provided as visual information such as characters or images, or as auditory information such as sound and audio.

The first and second wearing units 10 and 11 may be provided with the controllers 207 and 305, respectively. The controllers 207 and 305 may control operations of the first and second wearing units 10 and 11, respectively. However, for convenience, it will be described below that the first and second wearing units 10 and 11 are controlled by the controller 305 of the second wearing unit 11. The first wearing unit 10 may include the controller 207, and the second wearing unit 11 may not include the controller 305, although otherwise shown in drawings. That is, the controllers 207 and 305 may be provided in at least one of the first and second wearing units 10 and 11, and control the wearing units 10 and 11.

In this specification and drawings, first and second measurement signals mean measurement signals which are generated respectively. For example, the first measurement signal may mean a measurement signal generated by measuring a user's body part through the first measurer 200, and the second measurement signal may mean a measurement signal generated by measuring a user's body part through the second measurer 300, but not limited thereto.

Figure 4:
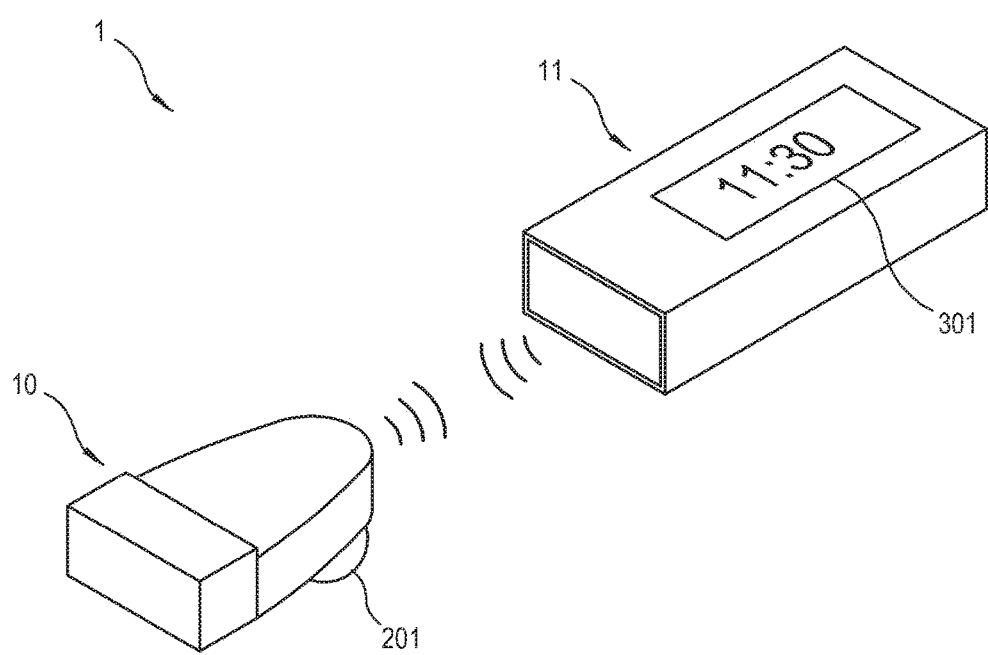
FIG. 4 illustrates an example of wireless communication and information exchange between the first and second wearing units according to an embodiment of the present disclosure.
Figure 5:
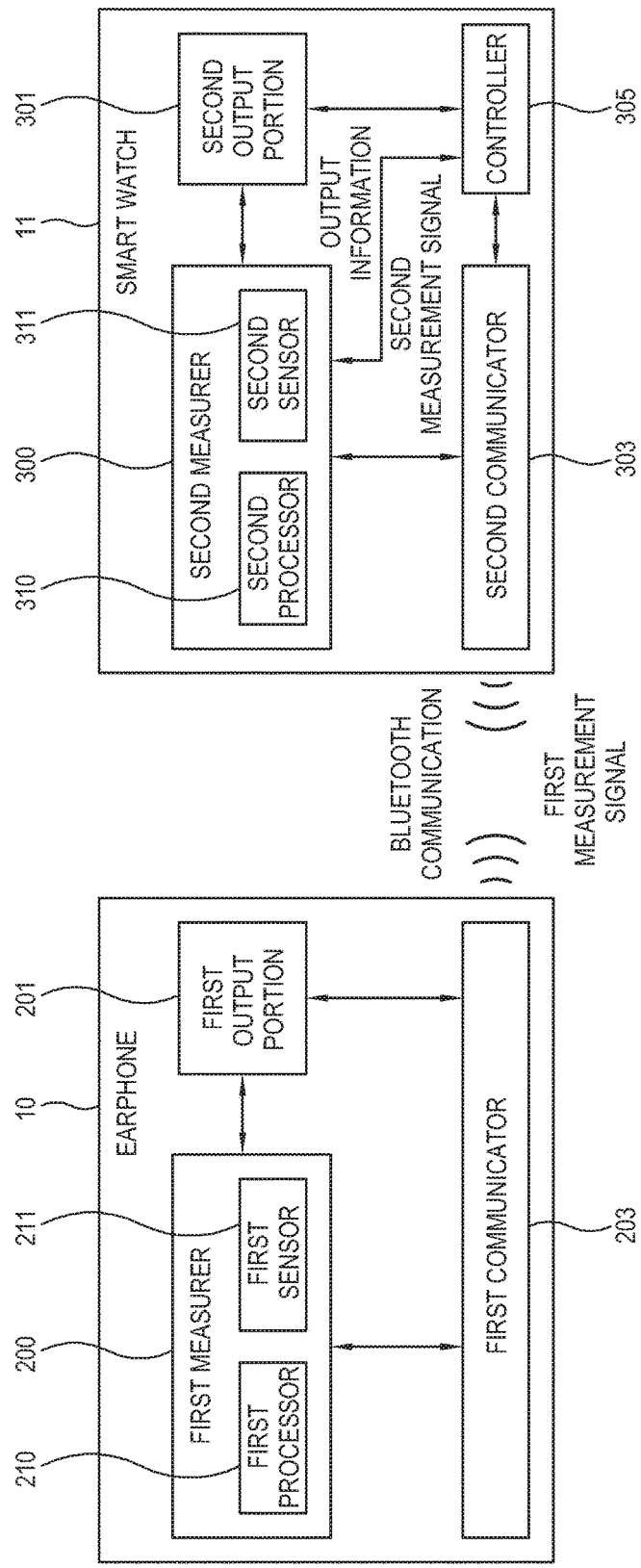
FIG. 5 illustrates an example of wireless communication and information exchange between the first and second wearing units according to an embodiment of the present disclosure.

FIGS. 4 and 5 illustrate examples of wireless communication performed by the first and second wearing units 10 and 11 to transmit and receive a measurement signal according to various embodiments of the present disclosure.

Referring to FIGS. 4 and 5, if the first and second wearing units 10 and 11 are disconnected from each other, each of the first and second wearing units 10 and 11 is configured to measure a vital sign from each of user's body parts wearing the first and second wearing units 11 and 12. As the controller 305 is positioned in the second wearing unit 11, the first wearing unit 10 measures the body part and generates a measurement signal and transmits the measurement signal to the second wearing unit 11 through the communicators 203 and 303.

The measurement signal generated by measuring a user's body through the first measurer 200 of the first wearing unit 10 is transmitted to the controller 305 of the second wearing unit 11 through the first and second communicators 203 and 303, and the measurement signal generated by measuring a user's body through the second measurer 300 of the second wearing unit 11 is also transmitted to the controller 305. The controller 305 receives the measurement signal from the second measurer 300, and analyzes a user's health status based on the measurement signal from the second measurer 300 and the measurement signal from the first wearing unit 10, collectively.

If the first and second wearing units 10 and 11 are disconnected from each other, vital signs are simultaneously measured from different body parts, and depending on the embodiment, different vital signs may be measured.

For example, the first measurer 200 may have the first sensor 211 therein including an electrode to measure the inside of an ear and may measure a user's brain wave, while the second measurer 300 may measure a heart rate variability (HRV) by measuring a pulsation of a wrist. The electronic apparatus 1 may analyze a user's sleeping phase, auditory reaction, etc. by measuring a brain wave and HRV.

The first and second measurers 200 and 300 are configured to measure different vital signs, or to measure the same vital sign and supplement each other. For example, if the second measurer 300 measures a user's heart and a detected HRV is great, it may be determined that a user's exercising. In such case, the controller 305 may temporarily suspend the measurement of a brain wave by the first measurer 200. Also, vital signs measured by the first and second measurers 200 and 300 may be compared with each other and thus any abnormal peak which may arise from malfunction may be excluded from analysis. If the quality of a signal measured by one of the measurers 200 and 300 during a certain period is determined to be lower than that of a signal measured by the other one of the measures 200 and 300, the signal with the higher quality during the certain period may replace the signal with the lower quality.

FIG. 4 illustrates an example of transmitting and receiving information between the first and second wearing units 10 and 11 through wireless communication. FIG. 5 is a block diagram showing a process of transmitting measurement signals of the first wearing unit 10 and the second wearing unit 11.

The measurement signal measured by the first measurer 200 is transmitted to the controller 305 through the first and second communicators 203 and 303, and the measurement signal measured by the second measurer 300 is also transmitted to the controller 305. The controller 305 analyzes a user's health status by processing the measurement signal, provides output information to the output portions 201 and 301 and controls the output portions 201 and 301 to provide a user with health information.

Referring to FIG. 5, the first measurement signal generated by the first measurer 200 is transmitted to the controller 305 through BT communication between the first and second communicators 203 and 303, and the second measurement signal generated by the second measurer 300 is transmitted to the controller 305, and the controller 305 analyzes the first and second measurement signals and transmits output information to the second output portion 301. The controller 305 may also transmit the output information to the first output portion 201 through the second communicator 303.

Figure 6:
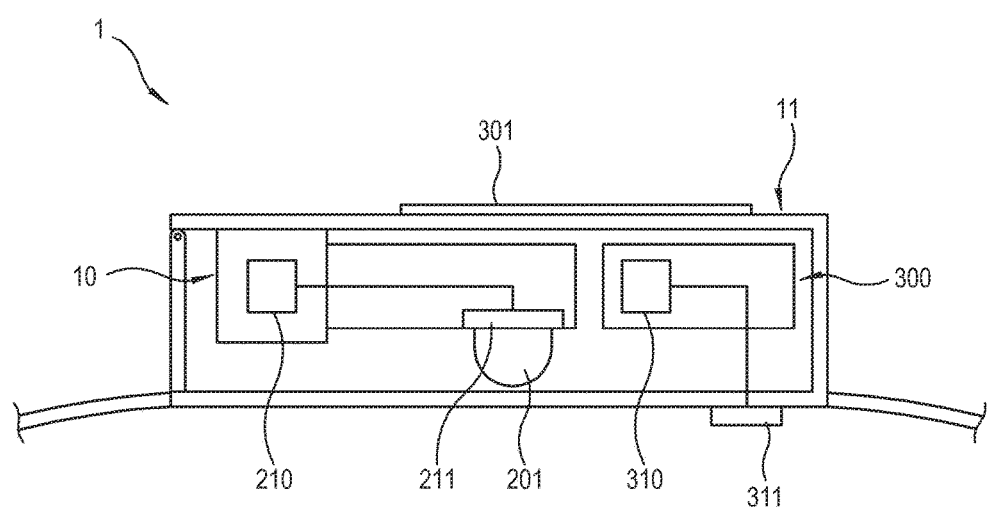
FIG. 6 illustrates an example of using a sub-processor of the first wearing unit while the first and second wearing units are connected to each other according to an embodiment of the present disclosure.
Figure 7:
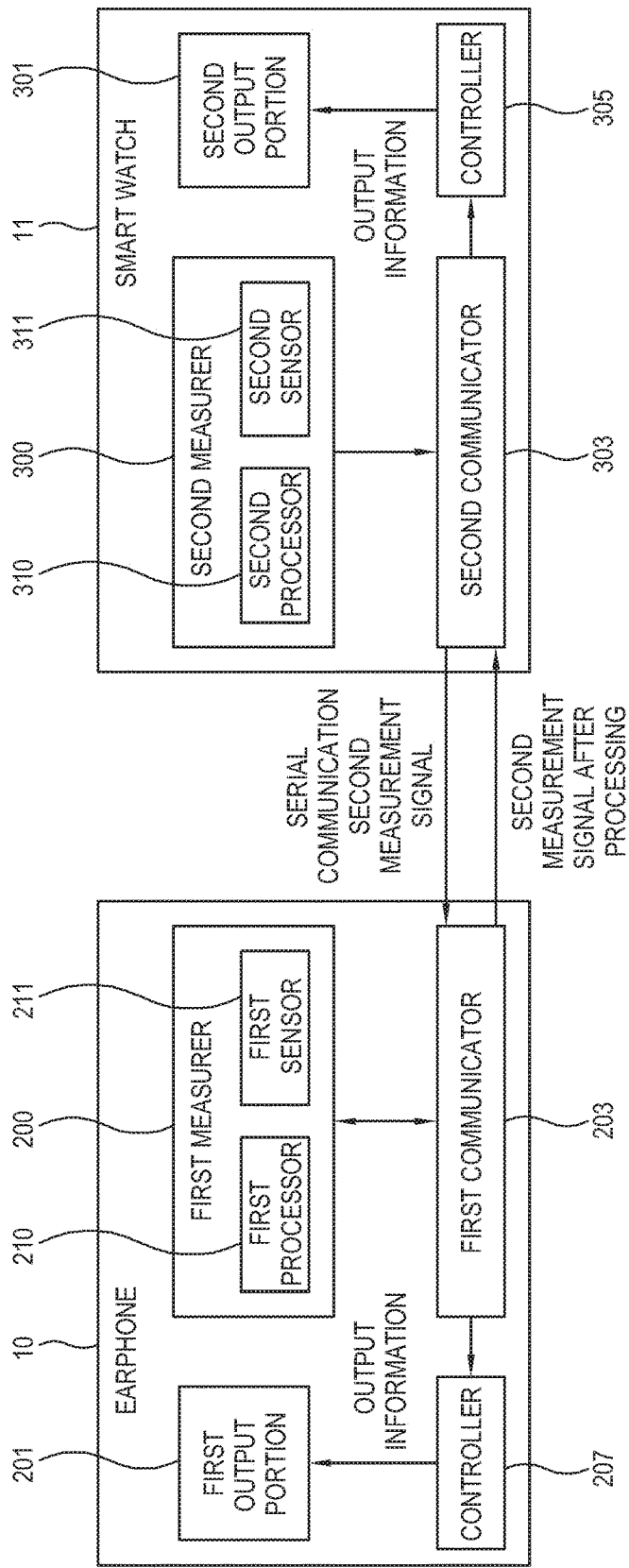
FIG. 7 is a block diagram showing an example of using the processor of the first wearing unit while the first and second wearing units are connected to each other according to an embodiment of the present disclosure.

FIGS. 6 and 7 illustrate an example of connecting the first and second wearing units 10 and 11 and using the processor of the first measurer according to various embodiments of the present disclosure.

Referring to FIGS. 6 and 7, if the first and second wearing units 10 and 11 are connected to each other and exchange information with each other through serial communication, power consumption and delay are less than when the first and second wearing units 10 and 11 perform wireless communication, and no frequency band is consumed and thus a more efficient communication is possible. If the first processor 210 of the first measurer 200 has greater performance than the second processor 310 of the second measurer 300, the controller 305 may control the first processor 210 of the first wearing unit 10 to process the signal measured by the second sensor 311 of the second measurer 300 if it is determined that the first wearing unit 10 is connected to the second wearing unit 11.

If the first and second wearing units 10 and 11 are connected to each other, the electronic apparatus 1 may measure a vital sign from a part of the user's body. In this embodiment, the first sensor 211 of the first measurer 200 is accommodated in the second wearing unit 11 not to be used.

In the embodiment, the controller 305 may use the first processor 210 of the first measurer 200 to process a sensing signal measured by the second sensor 311 of the second measurer 300. The first processor 210 of the first measurer 200 may include a high-performance amplifier, and when disconnected, may generate a more precise signal than a measurement signal generated by the second measurer 300.

In another embodiment, the controller 305 may use the second processor 310 of the second measurer 300 to process a sensing signal measured by the first sensor 211 of the first measurer 200. The second processor 310 of the second measurer 300 may include a low power amplifier, and when disconnected, may be driven with lower power than when only the first measurer 200 measures a body part.

When the first wearing unit 10 and the second wearing unit 11 are connected to each other, a vital sign may be measured from only a part of a user's body such as a user's wrist, and thus analysis of a user's health status using vital signs measured from a plurality of body parts of a user may not be performed. However, as an analog circuit may be shared by connecting the wearing units 10 and 11, a vital sign from a part of the user's body part may be precisely measured.

While the first and second wearing units 10 and 11 are connected to each other, the electronic apparatus 1 may be worn on a user's body part such as a wrist and may measure a body wave, electromyography (EMG), galvanic skin reflex (GSR), etc. and through the foregoing, analyze a quantity of a user's exercise, sleeping or non-sleeping and tiredness of a user.

FIG. 6 illustrates an example of storing the first sensor 211 of the first wearing unit 10 in the second wearing unit 11 and using only the first processor 210 of the first wearing unit 10 while the first and second wearing units 10 and 11 are connected to each other.

Referring to FIG. 6, the second measurement signal measured by the second measurer 300 may be transmitted to the first measurer 200 through the second communicator 303 and the first communicator 203, and the first measurer 200 may process the second measurement signal and transmit the processed signal to the controller 305. The controller 305 may process and analyze the second measurement signal and generate output information, and provide the output information to the second output portion 301. Since the first and second wearing units 10 and 11 are in the connected status, the output information may not be transmitted to the first output portion 201.

Figure 8:
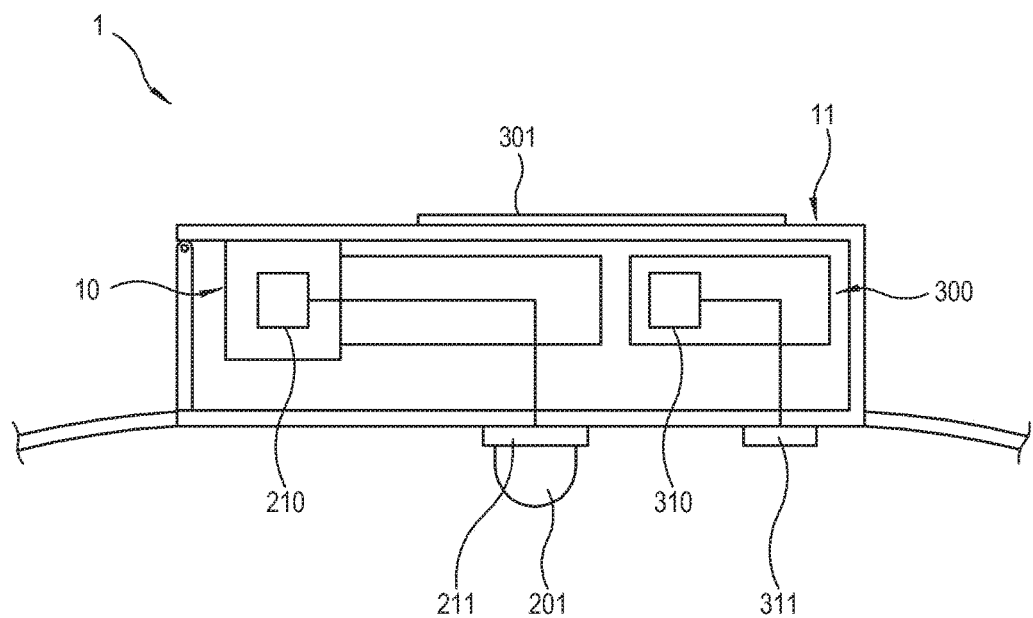
FIG. 8 illustrates an example of using the processor and sensor of a first measurer while the first and second wearing units are connected to each other according to an embodiment of the present disclosure.
Figure 9:
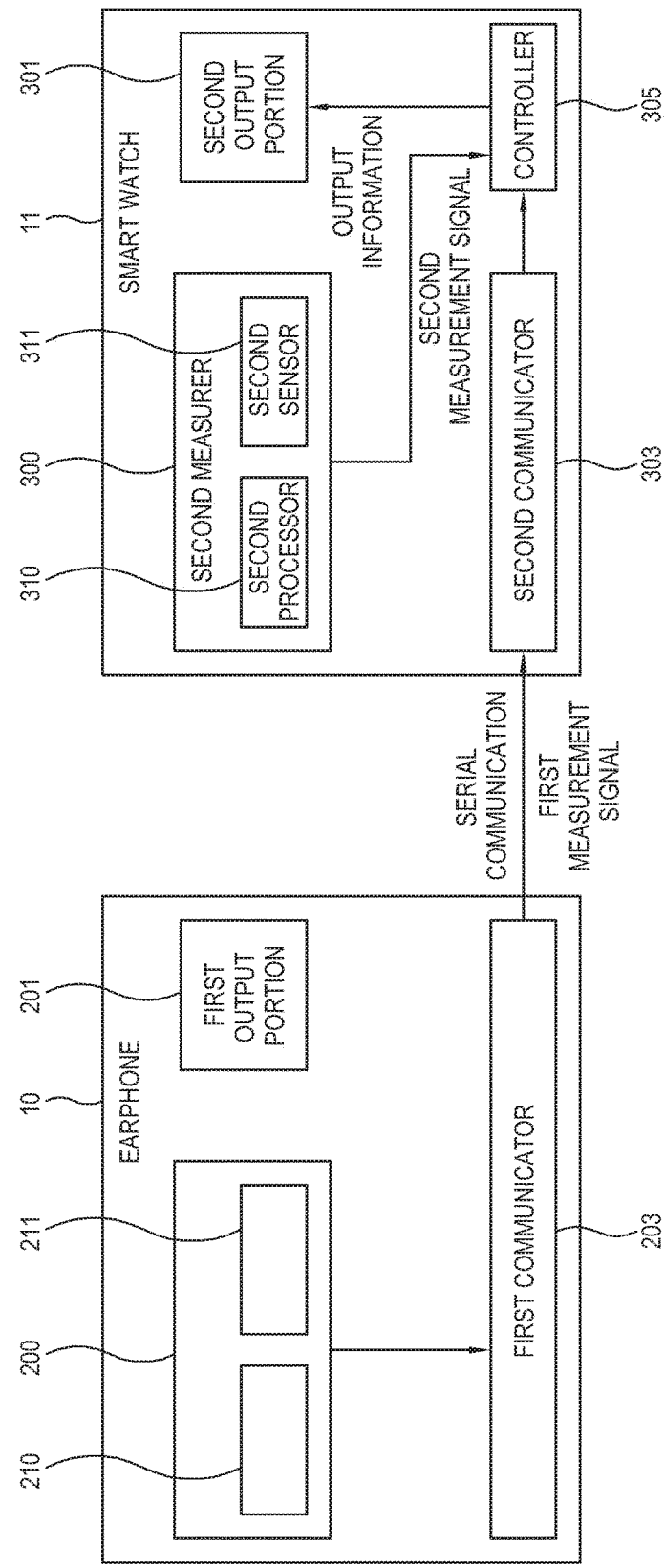
FIG. 9 is a block diagram showing an example of using the processor and the sensor of the first measurer while the first and second wearing units are connected to each other according to an embodiment of the present disclosure.

Unlike the case shown in FIG. 7, the first measurement signal measured by the first measurer 200 may be transmitted to the second measurer 300 through the first communicator 203 and the second communicator 303, and then processed by the second measurer 300 to be transmitted to the controller 305. The controller 305 may process and analyze the first measurement signal and generate output information, and provide the output information to the first output portion 201 or the second output portion 301. FIGS. 8 and 9 illustrate an example of connecting the first and second wearing units 10 and 11 and using the sensor 211 and the first processor 210 of the first measurer 200.

If the first and second wearing units 10 and 11 are connected to each other and thus the [first sensor 211 and the] second sensors 311 of the first and second measurers 200 and 300 simultaneously measure a vital sign from a user's body part, various vital signs may be measured and measurement signals may be generated from a single body part as the plurality of sensors 211 and 311 is used.

That is, two or more vital signs may be measured from a single body part of a user solely by the first sensor 211 of the first measurer 200 without a plurality of sensors being included in the second sensor 311 of the second measurer 300. Also, when the first and second wearing units 10 and 11 are connected to each other, the first sensor 211 of the first measurer 200 is available rather than being in an idle state and thus may measure vital signs from a user's body part, giving rise to reducing expenses that may incur when the plurality of sensors is provided in the second sensor 311 of the second measurer 300.

In the case of measuring a signal such as a body wave, a stable contact between an electrode and the human skin is important, and an element similar to an earphone sensor which is made of a convenient material may be provided in the first sensor 211 of the first measurer 200 and a vital sign from a user's wrist may be measured through the first sensor 211 of the first measurer 200 without repeatedly providing the earphone sensor in the second sensor 311 of the second measurer 300.

In this embodiment, the controller 305 of the second wearing unit 11 controls the wearing units 10 and 11, but not limited thereto. Alternatively, the controller 207 may be provided in the first wearing unit 10, and process information provided by the second wearing unit 11 and control the first output portion 201 to provide the processed information to a user, as described above.

Referring to FIGS. 8 and 9, the first measurement signal generated by the first measurer 200 after the measurement of a user's body is transmitted to the controller 305 through serial communication, and the second measurement signal generated by the second measurer 300 is transmitted to the controller 305. The second measurement signal may be directly transmitted to the controller 305, or as described with reference to FIGS. 6 and 7, may be transmitted to the first measurer 200 and processed by the first processor 210 to be transmitted to the controller 305 again. If the first processor 210 uses module with a higher performance than the second processor 310 does, signals may be effectively processed.

Figure 10:
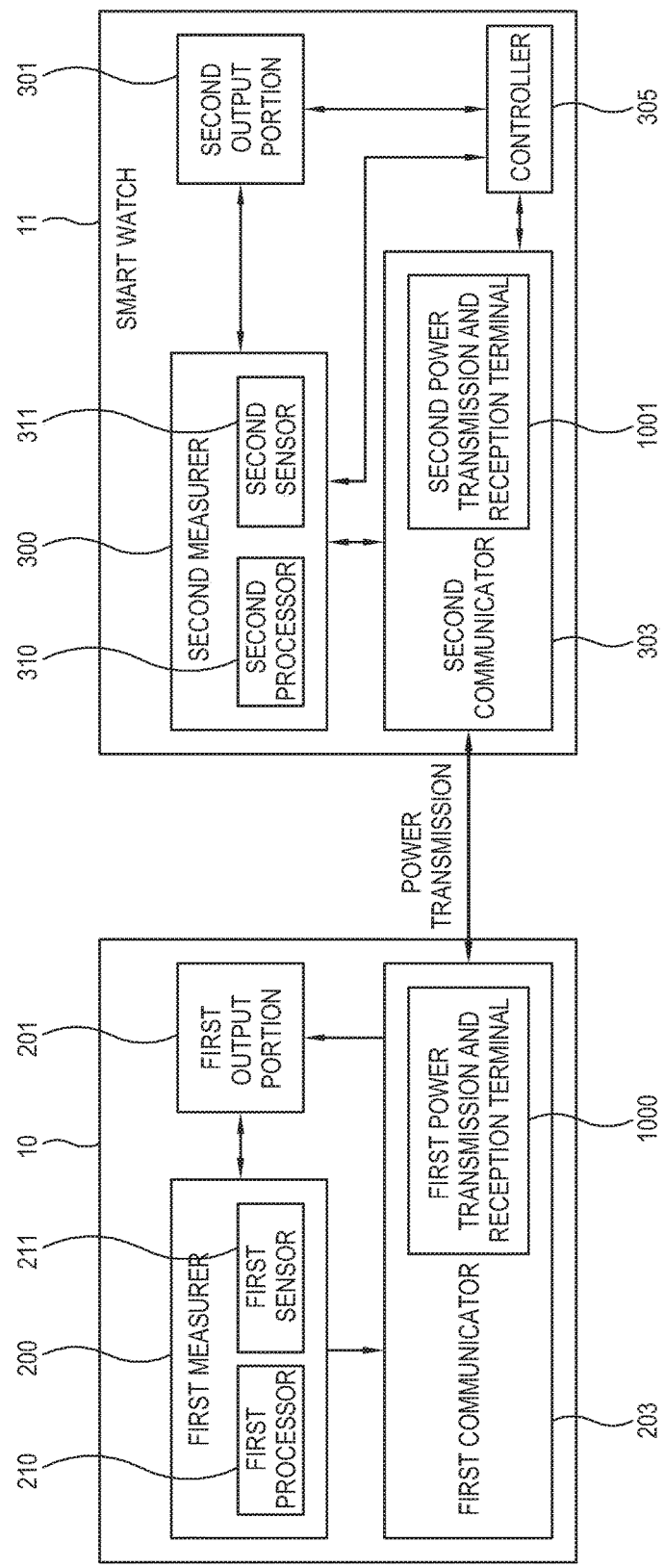
FIG. 10 illustrates an example of transmitting and receiving power between the first and second wearing units according to an embodiment of the present disclosure.

FIG. 10 illustrates an example of transmitting and receiving power between the wearing units according to an embodiment of the present disclosure.

Referring to FIG. 10, if the first wearing unit 10 and the second wearing unit 11 are simultaneously used, the size of batteries and battery consumption amount of the first and second wearing units 10 and 11 are different, and thus one of the first and second wearing units 10 and 11 should be separately connected to and charged by an external power source.

To resolve the foregoing inconvenience, the first and second communicators 203 and 303 according to an embodiment may include first and second power transmission and reception terminals 1000 and 1001, respectively, to exchange power therebetween when the first and second wearing units 10 and 11 are connected to each other. The first and second power transmission and reception terminals 1000 and 1001 may exchange power therebewteen by being connected to each other through a signal line or by being directly connected to each other. The first and second wearing units 10 and 11 may operate through power supplied by a chargeable lithium-ion polymer (the "battery"), and the battery may be charged by power supplied by an external power source through the power transmission and reception terminals 1000 and 1001. The power transmission and reception terminals 1000 and 1001 may further include a connector to which a signal line or device of various specifications such as an USB whose charging pin is exposed to the outside, and a charger to charge the battery.

The first power transmission and reception terminal 1000 of the first wearing unit 10 and the second power transmission and reception terminal 1001 of the second wearing unit 11 may be connected to each other directly or through a signal line and exchange power therebetween by a control of the controller 305.

The first and second power transmission and reception terminals 1000 and 1001 according to another embodiment may be configured to transmit and receive power wirelessly. For example, an electromagnetic induction, for which power is transmitted by inducing a current to a coil by a magnetic field generated between primary and secondary coils that transmit power, or a magnetic resonance for which a current is induced by an electromagnetic resonance that takes place by a wireless power signal between a power transmitter and a power receiver, or an electromagnetic radiation, for which power is transmitted wirelessly to the outside as an electromagnetic wave is radiated may be used.

If power is wirelessly exchanged between the first and second wearing units 10 and 11, the first and second wearing units 10 and 11 may share and use power even in the case where they are not connected to each other. In such case, one of the first and second wearing units 10 and 11 may further include a power receiver, and may not include an additional battery.

According to another embodiment, the first and second wearing units 10 and 11 may include a data packet to be transmitted by modulating power transmitted wirelessly. This is a modified embodiment of power line communication, and power is modulated to include data, and the modulated power is transmitted to a receiver, and the receiver may detect data included in the power by demodulating the power. Power modulation may include one of amplitude modulation, frequency modulation and phase modulation. In the case of amplitude modulation, the lowest level of power must be a minimum power level or higher as required by the receiver.

Figure 11:
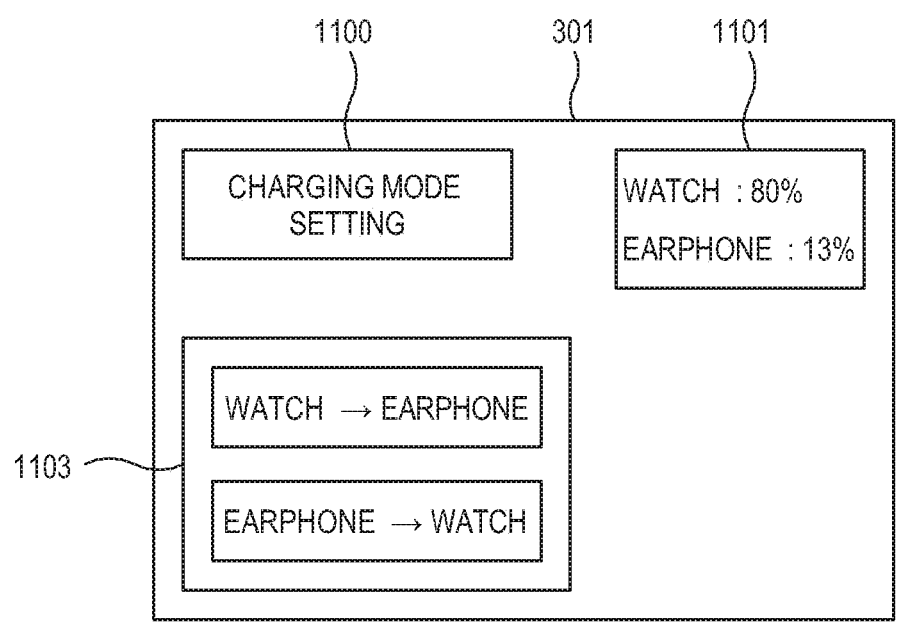
FIG. 11 illustrates a user interface (UI) provided for a user to charge a battery according to an embodiment of the present disclosure.

FIG. 11 illustrates a user interface (UI) which is provided to a user to charge the batteries of the first and second wearing units 10 and 11 according to an embodiment of the present disclosure.

Referring to FIG. 11, if the first and second wearing units 10 and 11 are connected to each other and a user selects a charging mode, the electronic apparatus 1 may provide a user with a UI including a notice 1100 notifying a user of the charging mode, a power status 1101 of the first and second wearing units 10 and 11 and a menu item 1101 for a user's selection, through the output portions 201 and 301.

If power is wirelessly transmitted and received according to another embodiment, the charging mode may be selected to transmit and receive power even if the first and second wearing units 10 and 11 are not connected to each other.

If the first and second wearing units 10 and 11 are connected to each other, the controller 305 may provide a user with a battery charging status of the first and second wearing units 10 and 11 through the output portions 201 and 301, and a user may confirm the battery charging status and select the charging mode through the UI.

The controller 305 controls the first and second power transmission and reception terminals 1000 and 1001 to transmit power from the first wearing unit 10 to the second wearing unit 11 or to transmit power from the second wearing unit 11 to the first wearing unit 10, based on a user command input through the UI.

The first and second wearing units 10 and 11 may be driven by receiving power from chargeable batteries, respectively. If certain time elapses after a user uses the first and second wearing units 10 and 11, levels of voltages of the batteries of the wearing units 10 and 11 may be different from each other due to a power consumption efficiency of the wearing units 10 and 11, the method of using the electronic apparatus 1 by a user, and characteristics of the batteries of the wearing units 10 and 11, respectively.

According to an embodiment, there may be a great difference between rates of remaining power of the first and second wearing units 10 and 11 (e.g. the first wearing unit: 13%; the second wearing unit: 80%) as shown in FIG. 11. In such case, a user may charge the battery of the earphone with the battery of the smart watch to use the earphone longer. For example, power may be supplied from the battery of the smart watch to the battery of the earphone until the quantity of power of the two devices becomes equal. Otherwise, if the remaining power of the earphone is greater than that of the smart watch, the battery of the smart watch may be charged by the battery of the earphone.

According to another embodiment, there may be a great difference between rates of remaining power of the first and second wearing units 10 and 11 (e.g. the first wearing unit: 13%; the second wearing unit: 80%) as shown in FIG. 11. In such case, a user may charge the battery of the smart watch with the battery of the earphone to use the smart watch longer. For example, a user may charge the battery of the smart watch until the remaining power of the battery of the earphone becomes zero.

According to another embodiment, power may be transferred by considering projected usage hours of the earphone as the first wearing unit 10 and the smart watch as the second wearing unit 11. As shown in FIG. 11, if the remaining power of the earphone as the first wearing unit 10 is 13% and the remaining power of the smart watch as the second wearing unit 11 is 80%, remained usage hours of the earphone and the smart watch may be calculated by considering a user's usage pattern. For example, if remained usage hours of the earphone is 27 hours and remained usage hours of the smart watch is 38 hours, the battery of the earphone may be charged by the battery of the smart watch.

The power transfer between the first and second wearing units 10 and 11 may be proceeded with by a method set by a user in advance when the first and second wearing units 10 and 11 are connected to each other. Otherwise, the power transfer between the first and second wearing units 10 and 11 may be proceeded with by a method determined by a user's input.

As described above, if the first and second wearing units 10 and 11 are connected to each other, power is transmitted and received through the first and second power transmission and reception terminals 1000 and 1001 between the first and second wearing units 10 and 11 to selectively charge one of the batteries of the first and second wearing units 10 and 11, and a UI including the menu item 1103 may be provided for a user to select power recharging through the output portions 201 and 301. That is, power may be transferred from the first wearing unit 10 to the second wearing unit 11 or from the second wearing unit 11 to the first wearing unit 10 by a user's selection.

The drawings and descriptions are just an example, and do not limit the scope of the present disclosure. The electronic apparatus 1 may be variously achieved to enable a plurality of apparatuses connected to each other to exchange power therebetween, and the UI for setting the foregoing is not limited to that shown in the drawings.

Figure 12:
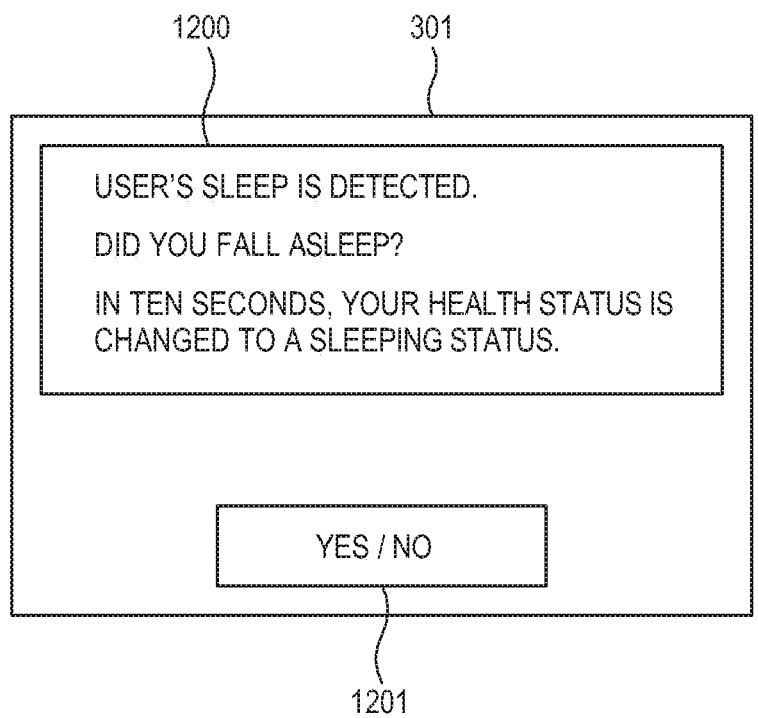
FIG. 12 illustrates an example of determining a user's health status according to an embodiment of the present disclosure.

FIG. 12 illustrates an example of determining a user's health status according to an embodiment of the present disclosure.

Referring to FIG. 12, the electronic apparatus 1 may measure a user's vital sign from a body part on which the first and second wearing units 10 and 11 are worn, and analyze the measured vital sign to analyze a user's health status. More specifically, the electronic apparatus 1 may measure and analyze a user's brain wave, heartbeat, pulse wave, etc. to thereby analyze a user's health status, i.e., whether a user is sleeping, is stressed or is exercising.

FIG. 12 illustrates an example of seeking confirmation from a user regarding whether a user is sleeping as one of the user's various health statuses.

The first and second measurers 200 and 300 measure user's vital signs from user's body parts on which the first and second measurers 200 and 300 are worn, respectively, and generate measurement signals. As described above, when the first and second wearing units 10 and 11 are disconnected from each other, they may measure a vital sign from a plurality of body parts and generate a measurement signal by supplementing each other. If the first and second wearing units 10 and 11 are connected to each other, they may share a circuit module, precisely measure a vital sign and generate a measurement signal.

The controller 305 may analyze a user's health status based on the signal generated and transmitted by the first and second measurers 200 and 300. The analysis of the health status may be implemented by comparing the signal and information stored in advance. For example, if a user's brain wave is consistent with a human brain wave during sleeping as stored in advance to a critical extent, it may be determined that a user is sleeping. If a user's heart rate rises to a critical level or higher, it may be determined that a user is exercising.

The controller 305 may determine a user's health status and seek confirmation from a user whether the analyzed result is correct. Referring to FIG. 12, a UI including a guide 1200 seeking confirmation from a user whether he/she is sleeping and a menu item 1201 corresponding to a user's selection is provided to a user through the output portions 201 and 301. Since a user may not see the UI if he/she is sleeping, the user's health status may be changed to a sleeping status after predetermined time elapses.

After the user's health status is changed to the sleeping status, the controller 305 may control overall operations of the electronic apparatus 1 based on the user's health status. For example, while a user is sleeping, the controller 305 may store a message, etc. transmitted by the outside, and if the user's health status is changed, the controller 305 may notify a user of the message, and may change to a mute mode not to output a sound through the output portions 201 and 301 such as a speaker.

Hereinafter, an example of the electronic apparatus 1 controlled as a user's health status is changed will be described with accompanying drawings.

Figure 13:
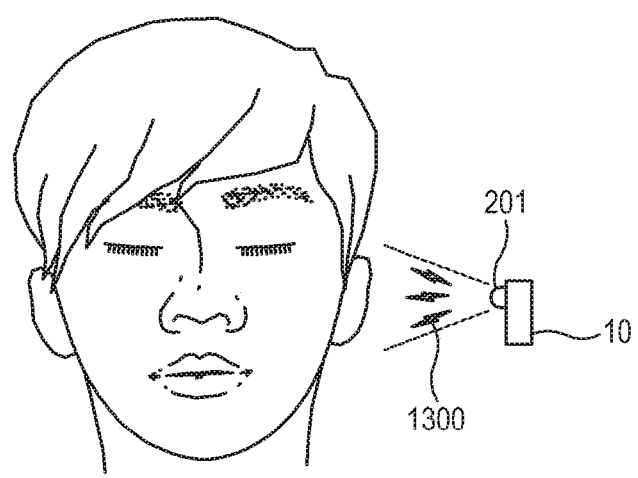
FIG. 13 illustrates an example of outputting a warning based on a user's health status as determined according to an embodiment of the present disclosure.

FIG. 13 illustrates an example of outputting a sound, etc. to a user based on a user's health status according to an embodiment of the present disclosure.

Referring to FIG. 13, the controller 305 may determine a user's health status based on a measurement signal measured by the measurers 200 and 300, and provide information based on the determined health status through the output portions 201 and 301.

If a user's health status is at risk, the controller 305 may warn a user of the foregoing. For example, if a user's health status is changed to a sleeping status while driving and if he/she is still in the sleeping status even after time set by a user elapses and if a user is distracted while studying and when it is necessary to call a user's attention, the controller 305 may output a warning sound 1300 through the output portions 201 and 301.

The sound 1300 may be set based on preset setting information, and a sound 1300 which varies depending on a change in a user's status may be output. For example, a sharp and uncomfortable, high level sound 1300 may be output to awake a user. If a user wants to sleep, a smooth and calm sound 1300 may be output, and if a user is distracted, a sound 1300 helping a user focus may be output.

The sound 1300 may be output through the earphone as the second wearing unit 11, or through the smart watch as the first wearing unit 10.

Figure 14:
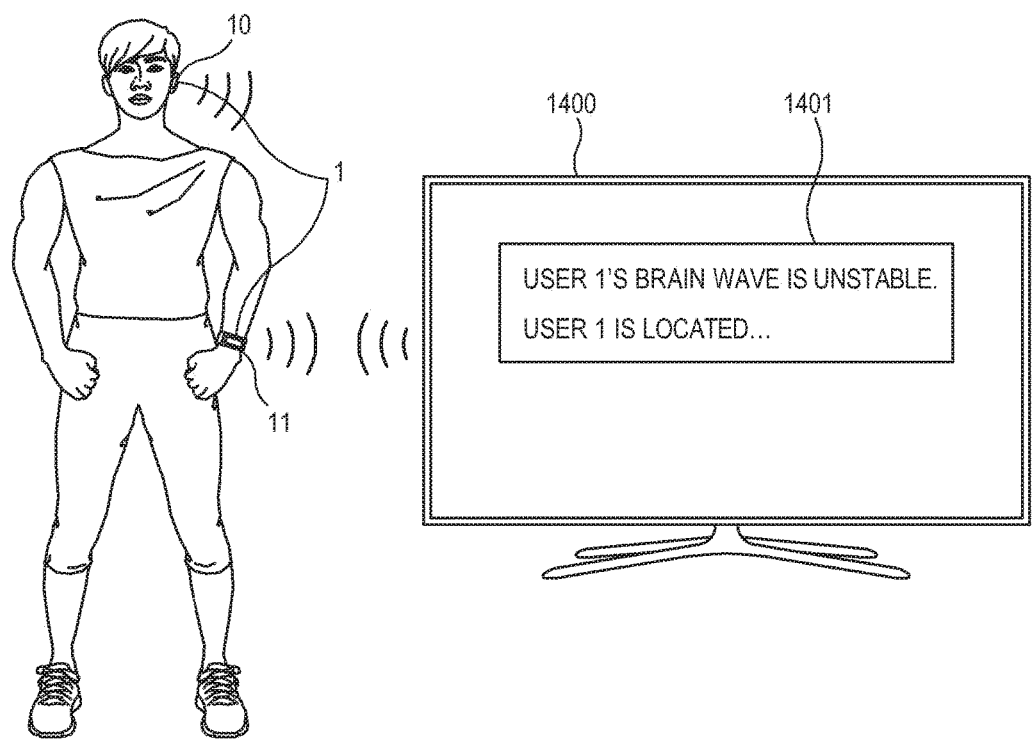
FIG. 14 illustrates an example of communicating with an external device based on a user's health status according to an embodiment of the present disclosure.
Figure 15:
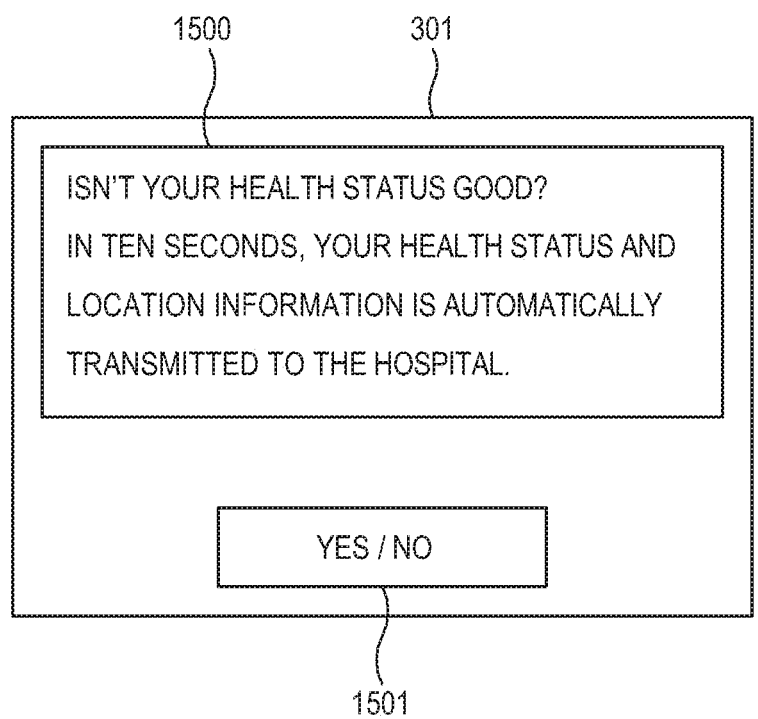
FIG. 15 illustrates a UI seeking confirmation from a user to communicate with an external device based on a user's health status according to an embodiment of the present disclosure.

FIGS. 14 and 15 illustrate examples of communicating with an external device based on a user's health status according to various embodiments of the present disclosure.

Referring to FIGS. 14 and 15, the electronic apparatus 1 may have the wearing units 10 and 11 including communicators 203 and 303 which are capable of communicating with an external device. The second wearing unit 11 which may be achieved by a smart watch may include a second communicator 303 which may communicate with the first wearing unit 10, and communicate with the outside through a communication network such as wireless LAN.

If the controller 305 determines that a user's status is at risk, based on a measurement signal, the controller 305 may notify the outside of the user's risky status through the second communicator 303.

For example, if a user blacks out or other similar problems arise, the controller 305 may communicate with, and notify, an external device 1400 of a hospital or rescue party that a user's status is unstable, and may transmit a user's location 1401 using global positioning satellite (GPS), as shown in FIG. 14.

Referring to FIG. 15, if the controller 305 determines that there is a problem in a user's health based on a measurement signal, the controller 305 outputs a UI including a guide 1500 to confirm the problem and a menu item 1501 seeking a user's approval, through the output portions 201 and 301.

A user may press YES and approve that he/she has a problem with his/her health, or press No to refuse to grant approval through the UI. If a user does not approve or refuse to approve even after predetermined time elapses, the controller 305 may determine that there is a problem in a user's health status and provide the external device 1400 with the user's health status and location information.

As shown therein, the electronic apparatus 1 may notify that a user's health is at risk, and may measure a user's vital sign in a daily life and transmit accumulated data such as a user's ECG, PPG, etc. and transmit such information to the outside so that the outside may determine whether a user has a heart disease. A heart disease is not easily shown and may be discovered by an abnormal status which takes place in a daily life or while light exercise. Without a process of measuring such state at a hospital for a long time, a portable vital sign measuring device may measure, compress and store a user's vital sign and transmit the vital sign to the outside for analysis.

The outside such as a hospital may reinstate the compressed vital sign transmitted by a user and analyze whether a user has any disease or a recovery process from treatment, and diagnose a user's health by analyzing the vital sign and provide a user with diagnostic information.

Figure 16:
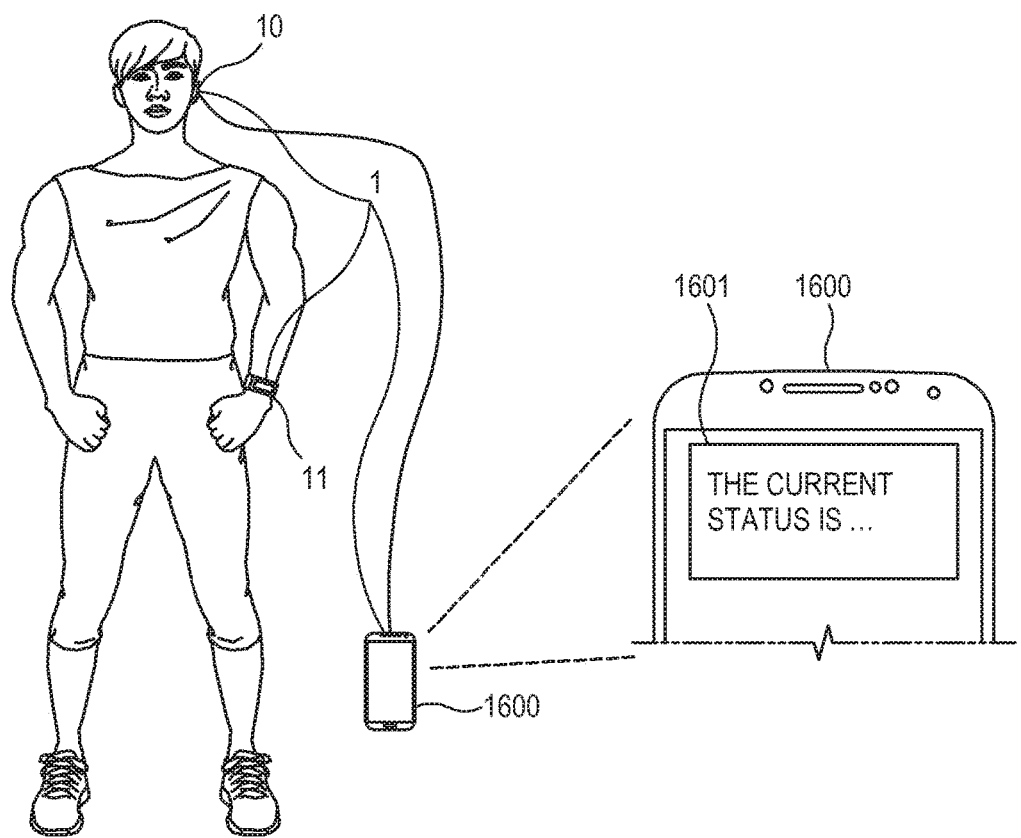
FIG. 16 illustrates an electronic apparatus according to an embodiment of the present disclosure.

FIG. 16 illustrates an electronic apparatus 1 according to an embodiment of the present disclosure.

Referring to FIG. 16, the electronic apparatus 1 according to the another embodiment of the present disclosure may include a portable device 1600 such as a smart phone, a first wearing unit 10 connected to the portable device 1600 in a wired manner, and a second wearing unit 11 worn on a user's body part.

The first and second wearing units 10 and 11 may measure a user's vital sign and transmit a measurement signal to the portable device 1600. The first wearing unit 10 is connected to the portable device 1600 through a signal line, and thus provides a measurement signal through wired communication, and the second wearing unit 11 may provide a measurement signal through wireless communication such as BT communication with the portable device 1600.

The portable device 1600 may analyze a received measurement signal to thereby analyze a user's health status, provide the analyzed information through a display 1601 of the portable device 1600, and provide output information through output portions 201 and 301 provided in at least one of the first and second wearing units 10 and 11.

The portable device 1600 may also provide a user's health information and location information to the outside according to a user's health status, and compress and store a vital sign measured in a daily life and transmit the vital sign to the outside periodically.

Then the outside may rescue a user based on the information provided by the portable device 1600, or diagnose a user's disease based on the user's vital sign and provide a user with diagnostic information.

Figure 17:
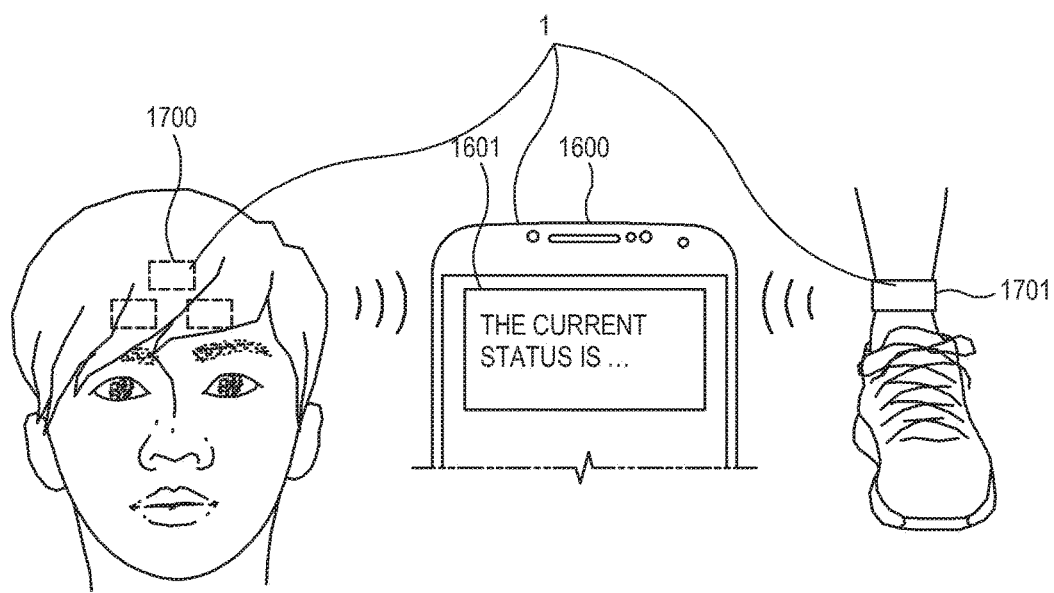
FIG. 17 illustrates an electronic apparatus according to an embodiment of the present disclosure.

FIG. 17 illustrates an electronic apparatus according to an embodiment of the present disclosure.

Referring to FIG. 17, the electronic apparatus 1 according to the another embodiment of the present disclosure may include a first wearing unit 1701 which is worn on a user's forehead and directly measures a brain wave as well as an earphone or smart watch, a second wearing unit 1701 which is worn on a user's ankle and measures a vital sign, and a portable device 1600 which receives a measurement signal from the first and second wearing units 10 and 11, analyzes the measurement signal, and provide the analyzed information through a display 1601.

The drawing is provided not to limit the scope of the present disclosure but to describe that the present disclosure may be variously achieved. The electronic apparatus 1 according to the present disclosure may be worn on various body parts and measure a user's vital sign, and analyze the measured vital sign and provide health information or diagnostic information to a user.

Figure 18:
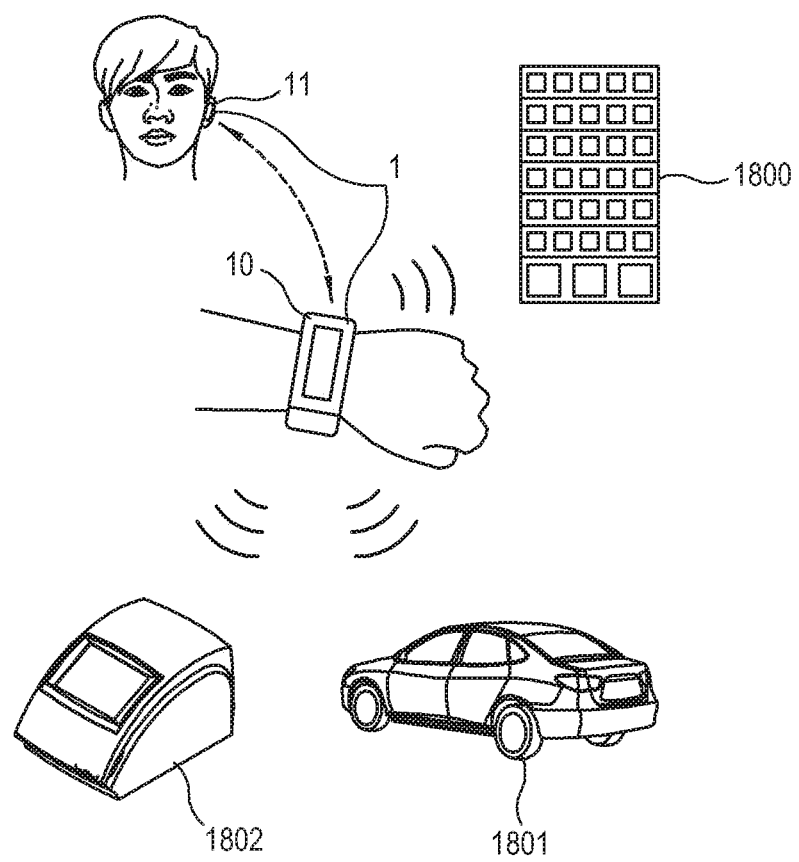
FIG. 18 illustrates an example of generating and using authentication information according to an embodiment of the present disclosure.

FIG. 18 illustrates an example of using a vital sign measured through the electronic apparatus as authentication information according to an embodiment of the present disclosure.

Referring to FIG. 18, a user's vital sign varies depending on personal biological characteristics of each user, and may be used to analyze a user's health status and may include each user's own information. External exposing information such as fingerprint, face recognition, voice and iris recognition may be used for authentication, or various vital signs including ECG, PPG and EMG may be used as authentication information.

In FIG. 18, the first and second wearing units 10 and 11 are provided to measure a user's vital sign, and the second wearing unit 11 may analyze a measurement signal and generate user authentication information and provide the generated authentication information to external devices 1800, 1801 and 1802 for authentication.

For example, if a user presses a button of a car 1801 to start the car 1801, an authentication module of the car 1801 may request the electronic apparatus 1 for authentication. Then, the controller 305 may analyze a measurement signal measured by the first and second wearing units 10 and 11 and generate authentication information, and may control the communicators 203 and 303 to provide the generated authentication information to the authentication module of the car 1801.

According to another embodiment, if a user performs commercial transaction, a point of sale (POS) machine 1802 may request the electronic apparatus 1 for authentication information to authenticate a user, and the electronic apparatus 1 may provide the authentication information to the POS machine 1802 based on a vital sign measured as requested. The POS machine 1802 may provide the user's authentication information to a bank, credit card company, etc. through a network to thereby complete the transaction with a user.

Figure 19:
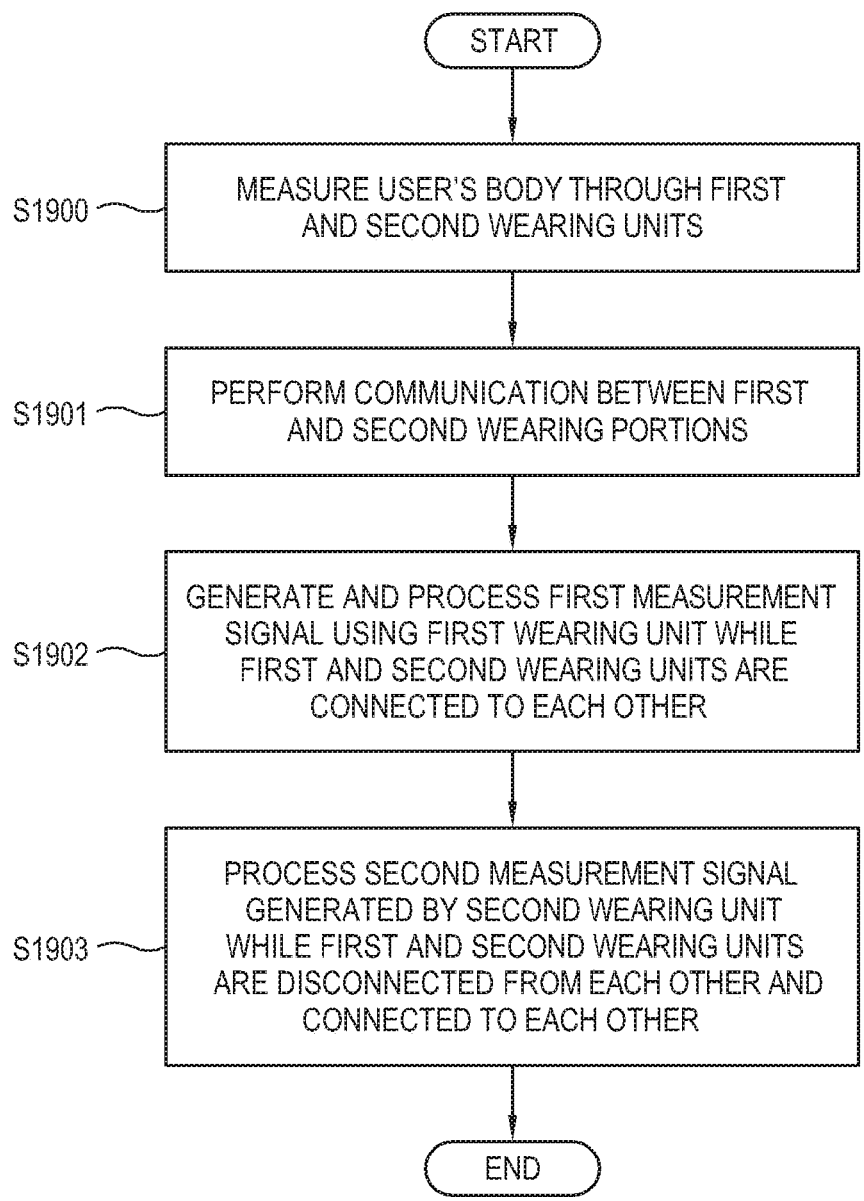
FIG. 19 is a flowchart of controlling the electronic apparatus according to an embodiment of the present disclosure.

FIG. 19 is a flowchart of the electronic apparatus 1 according to an embodiment of the present disclosure.

Referring to FIG. 19, at operation S1900, the first and second wearing units 10 and 11 measure a user's body and generate a measurement signal. At operation S1901, the first and second wearing units 10 and 11 communicate with each other to exchange information. At operation S1902, the controller 305 measures a user's body through the first wearing unit 10 and generates and processes a first measurement signal while the first and second wearing units 10 and 11 are connected. Lastly, at operation 51903, the controller 305 processes a second measurement signal generated by the second wearing unit 11 while the first and second wearing units 10 and 11 are disconnected from each other and connected to each other.

While the first and second wearing units 10 and 11 are disconnected from each other, the controller 305 may receive and process a measurement signal generated by the first measurer 200 and transmitted by the second communicator 303, and a measurement signal generated by the second measurer 300.

While the first and second wearing units 10 and 11 are connected to each other, the controller 305 may transmit a measurement signal generated by the second measurer 300 to the first measurer 300 to process the measurement signal through the first processor 210 of the first measurer 200, or process a measurement signal generated by the first measurer. That is, while the first and second wearing units 10 and 11 are connected to each other, the controller 305 may measure a vital sign more precisely through the second measurer 300 by using the first measurer 200 connected thereto, or control the first and second measurers 200 and 300 to simultaneously measure the same body part of a user.

FIG. 20 is a flowchart of the electronic apparatus 1 according to an embodiment of the present disclosure. At operation S2000, the controller 305 determines whether the first and second wearing units 10 and 11 are connected to each other. At operation S2001, if the first and second wearing units 10 and 11 are disconnected from each other, the first and second measurers 200 and 300 measure user's body parts on which the first and second measurers 200 and 300 are worn, and generate a measurement signal. At operation S2002, the measurement signal measured by the first measurer 200 is transmitted to the second wearing unit 11 through the first communicator 203. At operation S2003, the controller 305 processes and analyzes the measurement signal generated by the first measurer 200 and transmitted through the second communicator 303 and the measurement signal generated by the second measurer 300, and generates diagnostic information relating to a user's health status.

Referring to FIG. 20, at operation S2004, if the first and second wearing units 10 and 11 are connected to each other, the controller 305 measures a user's body part through the second measurer 300 by using the first measurer 200 and generates a measurement signal. At operation S2005, the controller 305 processes and analyzes the measurement signal generated by the second measurer 300 and generates diagnostic information relating to a user's health status.

At operation S2006, the controller 305 controls the output portions 201 and 301 to provide the generated diagnostic information.

If the first and second wearing units 10 and 11 are disconnected from each other and are worn on user's body parts, respectively, the measurers 200 and 300 respectively measure a vital sign from the worn locations and generate measurement signals. The controller 305 in this embodiment is located in the second wearing unit 11, and thus the measurement signal measured and generated by the first wearing unit 10 is transmitted to the controller 305 through the communicators 203 and 303. The measurement signal generated by the second measurer 300 may be directly transmitted to the controller 305, and the controller 305 may determine a user's health status based on the measurement signal.

If the first and second wearing units 10 and 11 are connected to each other, the electronic apparatus 1 measures a vital sign from the body part on which the second wearing unit 11 is worn, and generates the measurement signal, but may use the first measurer 200. More specifically, if the first and second wearing units 10 and 11 are connected to each other, the sensor 211 of the first measurer 200 may be used or may be accommodated in the second wearing unit 11. If the sensor 211 of the first measurer 200 is accommodated in the second wearing unit 11, the first measurer 200 may be used to cause the first processor 210 of the first measurer 200 to process the signal measured by the sensor 311 of the second measurer 300. If the sensor of the first measurer 200 is used, the first and second measurers 200 and 300 may simultaneously measure a vital sign from the same body part and generate a measurement signal.

In this embodiment, the first measurer 200 may include the first processor 210 with higher performance than the second measurer 300 does, and as the first and second wearing units 10 and 11 are connected to each other, the second wearing unit 11 may measure and process a vital sign more precisely by using the first processor 210 with high performance which is included in the first measurer 200.

As described above, the electronic apparatus according to the present disclosure may measure a user's vital sign from a plurality of body parts, accurately analyze a user's health status and provide a user with related information.

While the present disclosure been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic apparatus which is capable of being worn on a user's body, the electronic apparatus comprising:
   a first wearing device and a second wearing device configured to connect to each other,
   wherein the first wearing device comprises:
      a first sensor configured to measure a first vital signal from the user's body,
      a first amplifier, and
      a first communicator configured to communicate with the second wearing device, and
   wherein the second wearing device comprises:
      a second sensor configured to measure a second vital signal from the user's body,
      a second amplifier, and
      a second communicator configured to communicate with the first wearing device; and
   at least one main processor configured to:
      based on the first wearing device and the second wearing device being disconnected from each other, control the first amplifier to amplify the measured first vital signal and generate a first measurement signal based on the amplified first vital signal, and control the second amplifier to amplify the measured second vital signal and generate a second measurement signal based on the amplified second vital signal, respectively, and
      based on the first wearing device and the second wearing device being connected to each other, control the first amplifier to amplify the measured second vital signal and generate a third measurement signal based on the amplified second vital signal.

2. The electronic apparatus according to claim 1,
   wherein each of the first sensor and the second sensor are configured to generate a sensing signal by measuring the user's body; and
   wherein each of the first sensor and the second sensor comprises a sub-processor configured to process the sensing signal to generate at least one of the first measurement signal and second measurement signal.

3. The electronic apparatus according to claim 2, wherein the sub-processor comprises an amplifier configured to amplify the sensing signal.

4. The electronic apparatus according to claim 1, wherein at least one of the first vital signal and the second vital signal comprises at least one of electroencephalogram (EEG), electrocardiogram (ECG), photo plethysmography (PPG), electromyogram (EMG), or galvanic skin reflex (GSR).

5. The electronic apparatus according to claim 1, further comprising an output portion configured to output information.

6. The electronic apparatus according to claim 5, wherein the output portion is provided in at least one of the first wearing device and the second wearing device.

7. The electronic apparatus according to claim 5, wherein the output portion comprises a display configured to display an image corresponding to the information.

8. The electronic apparatus according to claim 5, wherein the output portion comprises a speaker configured to output sound corresponding to the information.

9. The electronic apparatus according to claim 5, wherein the at least one main processor is further configured to:
compare information on at least one of the first measurement signal or the second measurement signal with a predetermined information on a critical value, and generate diagnostic information on the user's health status based on comparison result, and
control the output portion to provide the generated diagnostic information.

10. The electronic apparatus according to claim 9, wherein the user's health status comprises the user's sleeping status.

11. The electronic apparatus according to claim 10, wherein the at least one main processor controls the output portion to warn that the user is asleep.

12. The electronic apparatus according to claim 5, wherein the at least one main processor controls the output portion to provide a user interface (UI) comprising menu items for a user to change setting information of the electronic apparatus.

13. The electronic apparatus according to claim 5, wherein at least one of the first communicator and the second communicator is capable of communicating with an external device.

14. The electronic apparatus according to claim 13, wherein the at least one main processor controls the output portion to provide information transmitted from the outside.

15. The electronic apparatus according to claim 1,
wherein each of the first communicator and the second communicator comprises a terminal to supply or receive power, and
wherein the at least one main processor controls the first communicator and the second communicator to exchange power between the first wearing device and second wearing device when the first wearing device and the second wearing device are connected to each other.

16. The electronic apparatus according to claim 1, wherein the at least one main processor generates user authentication information based on the first measurement signal and the second measurement signal.

17. The electronic apparatus according to claim 16, wherein the at least one main processor controls at least one of the first communicator and the second communicator to transmit the authentication information to an external device in response to a request for authentication from the external device.

* * * * *